United States Patent
Jo

(10) Patent No.: US 6,253,104 B1
(45) Date of Patent: Jun. 26, 2001

(54) METHOD OF PREPARING PHARMACEUTICAL MOXA EXTRACT AND APPARATUS FOR ELECTRICAL MOXIBUSTION USING THE SAME EXTRACT

(75) Inventor: Bong Kwon Jo, Pusan (KR)

(73) Assignee: Kijang Medical Co., Pusan (KR)

(*) Notice: Subject to any disclaimer, the term of this patent is extended or adjusted under 35 U.S.C. 154(b) by 0 days.

(21) Appl. No.: 09/401,733

(22) Filed: Sep. 23, 1999

(30) Foreign Application Priority Data

Sep. 26, 1998 (KR) .................................. 98-40122
Aug. 28, 1999 (KR) .................................. 99-36073

(51) Int. Cl.⁷ ...................................................... A61N 1/30
(52) U.S. Cl. ............................................................ 604/20
(58) Field of Search ................................ 424/195.1, 400; 514/783; 604/19, 20, 289–291, 304, 307

(56) References Cited

U.S. PATENT DOCUMENTS

| | | | |
|---|---|---|---|
| 3,946,733 | * | 3/1976 | Han . |
| 4,203,438 | * | 5/1980 | Shiu . |
| 4,604,088 | * | 8/1986 | Nottbohm . |
| 4,657,531 | * | 4/1987 | Choi . |
| 4,671,788 | * | 6/1987 | Wu . |
| 4,693,711 | * | 9/1987 | Bremer et al. . |
| 4,747,841 | | 5/1988 | Kuratomi et al. ............... 1/1 |
| 5,549,960 | * | 8/1996 | Yoo . |
| 5,772,688 | * | 6/1998 | Muroki . |
| 5,902,518 | * | 5/1999 | Khazai et al. . |
| 5,904,664 | * | 5/1999 | Kim . |
| 5,948,506 | * | 9/1999 | Yoo . |

* cited by examiner

Primary Examiner—Richard K. Seidel
Assistant Examiner—Catherine Serke
(74) Attorney, Agent, or Firm—Merchant & Gould P.C.

(57) ABSTRACT

The present invention relates to a method of preparing pharmaceutical Moxa extract and a skin-electrode type electrical moxibustion apparatus, and more particularly to method and apparatus of making Artemisia-extract tincture and Artemisia-extract lotion in a simple manner and operation moxibustion remedy in a convenient manner.

The present invention provides a method of preparing the pharmaceutical Moxa extract which extracts Artemisia-methanol extract or Artemisia-ethyl acetate fraction from young leaves of the Artemisia, and then makes the Artemisia-extract tincture or the Artemisia-extract lotion; and an apparatus for electrical moxibustion which comprises a heating unit for generating heat at a certain temperature when power is applied through cable from outside thereto, a fixing unit for fixing and supporting the heating unit and indirectly transferring heat from the heating unit to the skin, an adiabatic unit for preventing heat from being scattered to upper and side directions by forming a housing surrounding all upper and sides of the heating unit and the fixing unit, and a removable moxibustion pad to be attached and detached to the fixing unit.

13 Claims, 7 Drawing Sheets

METHOD OF PREPARING PHARMACEUTICAL MOXA EXTRACT AND APPARATUS FOR ELECTRICAL MOXIBUSTION USING THE SAME EXTRACT

BACKGROUND OF THE INVENTION

1. Technical Field

The present invention relates to a method of preparing pharmaceutical Moxa extract with use of the moxa and an skin-electrode type electrical moxibustion apparatus for treating moxibustion with use of the pharmaceutical Moxa extract, and more particularly to a method of preparing pharmaceutical Moxa extract and an apparatus for electrical moxibustion in which the pharmaceutical Moxa extract are prepared by extracting pharmacological components from the moxa, and moxibustion can be easily operated onto the affected part with use of the pharmaceutical Moxa extract.

2. Description of the Prior Art

Conventional moxibustion remedies using moxa are classified into direct and indirect manners. However, such manners have troubles in that smoke is generated when burning the moxa lump and a user should light the moxa lump whenever operation the moxibustion. In addition, such manners can cause risks of burn in case that the moxa lump falls during the operation.

In addition, ashes on the afflicted part from the burning moxa lump should be removed after operation and an operator should look after the patient in a near position through the operation, which requires the operator to spend much time, so to cause higher expenses.

In order to overcome such problems, recently, technical development for pharmaceutical Moxa extract which can be easily and hygienically used becomes required for the moxibustion treatment instead of the moxa lump.

SUMMARY OF THE INVENTION

Therefore, an object of the present invention is to provide a method of preparing pharmaceutical Moxa extract having crude drug components of the moxa by extracting Artemisia extract from the moxa with use of simple solvent treatment process.

In addition, another object of the present invention is to provide an electrical moxibustion apparatus in which, after injecting the pharmaceutical Moxa extract, extracted and prepared from the moxa, into a liquid permeable membrane, a moxibustion pad can retain the liquid permeable membrane having the pharmaceutical Moxa extract, and in which moxibustion treatment can be easily operated by attaching the skin-electrode type electrical moxibustion apparatus on the affected parts.

Further, still another object of the present invention is to provide an electrical moxibustion apparatus in which the pharmaceutical Moxa extract, extracted and prepared from the moxa, is applied on the affected parts and then heated indirectly by an electrical heater such that crude drug components of the moxa can be naturally permeated into the skin.

For obtaining the objects, the first embodiment of the present invention provides a method of preparing pharmaceutical Moxa extract comprising the steps of: extracting Artemisia-methanol extract by extracting Artemisia methanol from young leaves of the Artemisia several times with use of methanol as a solvent, and condensing the Artemisia methanol; and preparing pharmaceutical Moxa extract by diluting or processing the Artemisia-methanol extract with a specific solvent.

In order to fulfill the above objects, the second embodiment of the present invention provides a method of preparing pharmaceutical Moxa extract comprising the steps of: extracting Artemisia-methanol extract by extracting Artemisia methanol from young leaves of the Artemisia several times with use of methanol as a solvent, and condensing the extract; extracting Artemisia-ethyl acetate fraction by suspending the Artemisia-methanol extract in water, then mixing the suspended extract with ethyl acetate, and then distilling the mixture with use of a fractional distiller; and preparing pharmaceutical Moxa extract by diluting or processing the extracted Artemisia-ethyl acetate fraction with a specific solvent.

For achieving the objects, the third embodiment of the present invention provides method of preparing pharmaceutical Moxa extract comprising the steps of: extracting Artemisia-methanol extract by extracting Artemisia methanol from young leaves of the Artemisia several times with use of methanol as a solvent, and condensing the extract; extracting Artemisia-dichloromethane fraction, separated in a lower portion of a fractional distiller, by suspending the Artemisia-methanol extract in water, then mixing the suspended extract with dichloromethane, and then distilling the mixture with use of the fractional distiller; extracting Artemisia-ethyl acetate fraction, separated in an upper portion of the fractional distiller, by mixing the residuals, after extracting the Artemisia-dichloromethane fraction, with ethyl acetate, and then distilling the mixture with use of the fractional distiller; and preparing pharmaceutical Moxa extract by mixing and condensing the extracted Artemisia-dichloromethane fraction and Artemisia-ethyl acetate fraction and then diluting or processing the Artemisia-ethyl acetate fraction with a specific solvent.

In each embodiment, the Artemisia-methanol extract extracting step utilizes medicine-mixed moxa, made by mixing young leaves of the Artemisia with little medicinal stuffs, which is at least one selected from the group of consisting cinnamon cortex, dried ginger, clove, saussurea root, Korean aralia root, asarum, Angelicae Dahuricae root, orpiment, atractylis, myrrh, frankincense, akene, garlic, beeswax, and sulfur.

In addition, Artemisia-extract tincture can be made by evaporating the Artemisia-methanol extract, Artemisia-ethyl acetate fraction, or the mixture of the Artemisia-dichloromethane and the Artemisia-ethyl acetate fraction, and then diluting the dried with use of 2–5 times amount of ethanol relative to the weight of the dried.

On the other hand, Artemisia-extract lotion can be made by evaporating and then powdering the Artemisia-methanol extract, Artemisia-ethyl acetate fraction, or the mixture of the Artemisia-dichloromethane and the Artemisia-ethyl acetate fraction, and then mixing the powder with diluent such as vaseline, liquid paraffin, isostearic acid, stearyl alcohol, myristyl alcohol, and polyvinyl alcohol block copolymer.

In order to fulfill other objects of the present invention, another embodiment provides an apparatus for electrical moxibustion comprising: heating means for generating heat at a certain temperature when power is applied thereto; fixing means for fixing and supporting the heating means, the fixing means having first heat-transferring media for transferring heat from the heating means to skin indirectly; adiabatic means for preventing heat of the heating means from being dispersed to upper and side directions, the adiabatic means forming a housing surrounding all upper and side portions of the heating means and the fixing means; and moxibustion pad means removably mounted to the fixing means, the pad means being indirectly heated by heat transferred from the heating means through the first heat-transferring media, the pad means having a synthetic resin pad in a certain area for covering the affected part and second heat-transferring media which is removably fixed to the first heat-transferring media.

In order to achieving other objects, still another embodiment of the present invention provides an apparatus for electrical moxibustion comprising: heating means having two electrode terminals, which generates heat at a certain temperature when power is applied from the terminals; fixing means forming a case having a seating groove opened upwardly for seating the heating means thereon, the fixing means fixing and supporting the heating means safely with use of the case, the fixing means transferring heat from the heating means to skin indirectly, wherein the fixing means is formed by molding insulating materials with coating inside of the seating groove with insulating materials and seating the heating means upon the seating groove in order to be insulated from the heating means; and adiabatic means for preventing heat of the heating means from being dispersed to upper and side directions, the adiabatic means forming a housing surrounding all upper and side portions of the heating means and the fixing means.

In each embodiment of the apparatus for electrical moxibustion, a positive temperature coefficient (PTC) resistor, a conductive polymer heater made by mixing an electrical conductor such as carbon black into polymeric materials such as polyethylene or rubber, or a nichrome wire heater can be used.

BRIEF DESCRIPTION OF THE DRAWINGS

These and other features, aspects, and advantages of the present invention will become better understood with regard to the following description, appended claims, and accompanying drawings, in which like components are referred to by like reference numerals. In the drawings:

DETAILED DESCRIPTION OF THE PREFERRED EMBODIMENT

Hereinafter, a method of preparing pharmaceutical Moxa extract and an apparatus for electrical moxibustion according to each preferred embodiment of the present invention will be described in detail with reference to the accompanying drawings.

Figure 1:
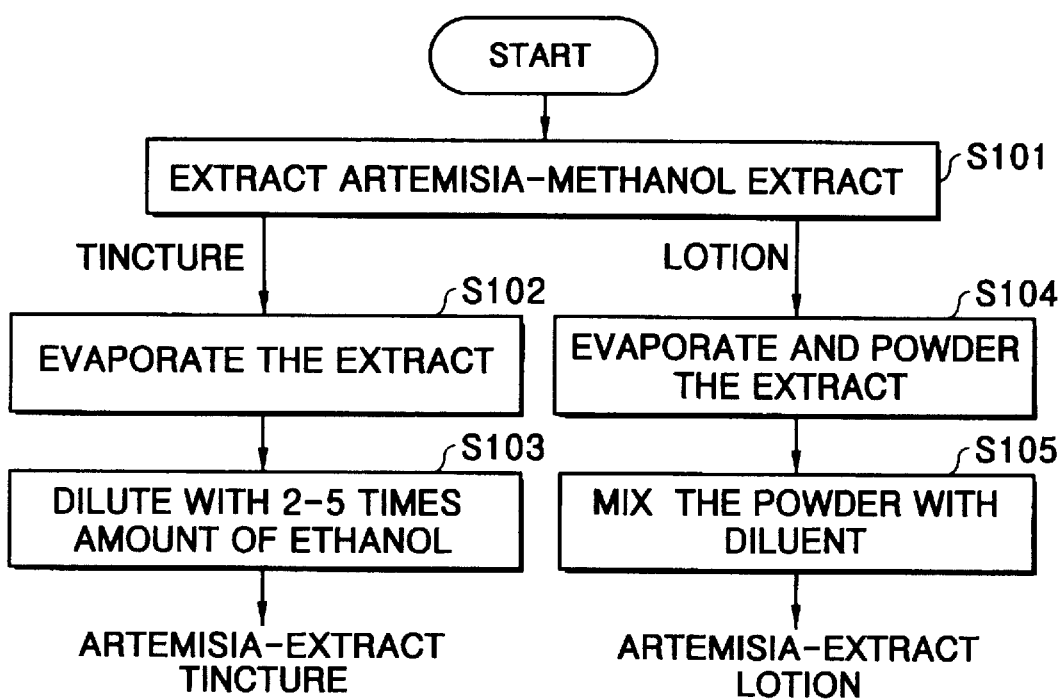
FIG. 1 is a flow chart for illustrating the first embodiment of the method of preparing pharmaceutical Moxa extract according to the present invention.

FIG. 1 is a flow chart showing one embodiment of the method of preparing pharmaceutical Moxa extract according to the present invention, which is composed of the steps of extracting Artemisia-methanol extract S1 01, and preparing the pharmaceutical Artemisia extract S102–105.

As shown in the figure, the step of extracting the Artemisia-methanol extract S101 obtains the Artemisia-methanol extract by putting young leaves of the Artemisia and methanol as an organic solvent, extracting Artemisia methanol therefrom, and then condensing the Artemisia methanol.

The steps of preparing the pharmaceutical Moxa extract S102, S103 may prepare the pharmaceutical Moxa extract from the Artemisia methanol extract. At this time, the obtained pharmaceutical Moxa extract is in the form of having color but not leaving remnants after applied on the skin. Particularly, after evaporating the Artemisia-methanol extract S102, Artemisia-extract tincture, which is possibly applied on the skin in a liquid state, can be made by diluting the dried Artemisia-methanol extract with use of 2–5 times amount of ethanol relative to the weight of the dried Artemisia-methanol extract S103.

On the other hand, the steps of preparing the pharmaceutical Moxa extract S104, S105 may make Artemisia-extract lotion, which is possibly applied on the skin, by evaporating the extracted Artemisia-methanol extract, then powdering the dried Artemisia-methanol extract S104, and mixing the powder with diluent S105.

Figure 2:
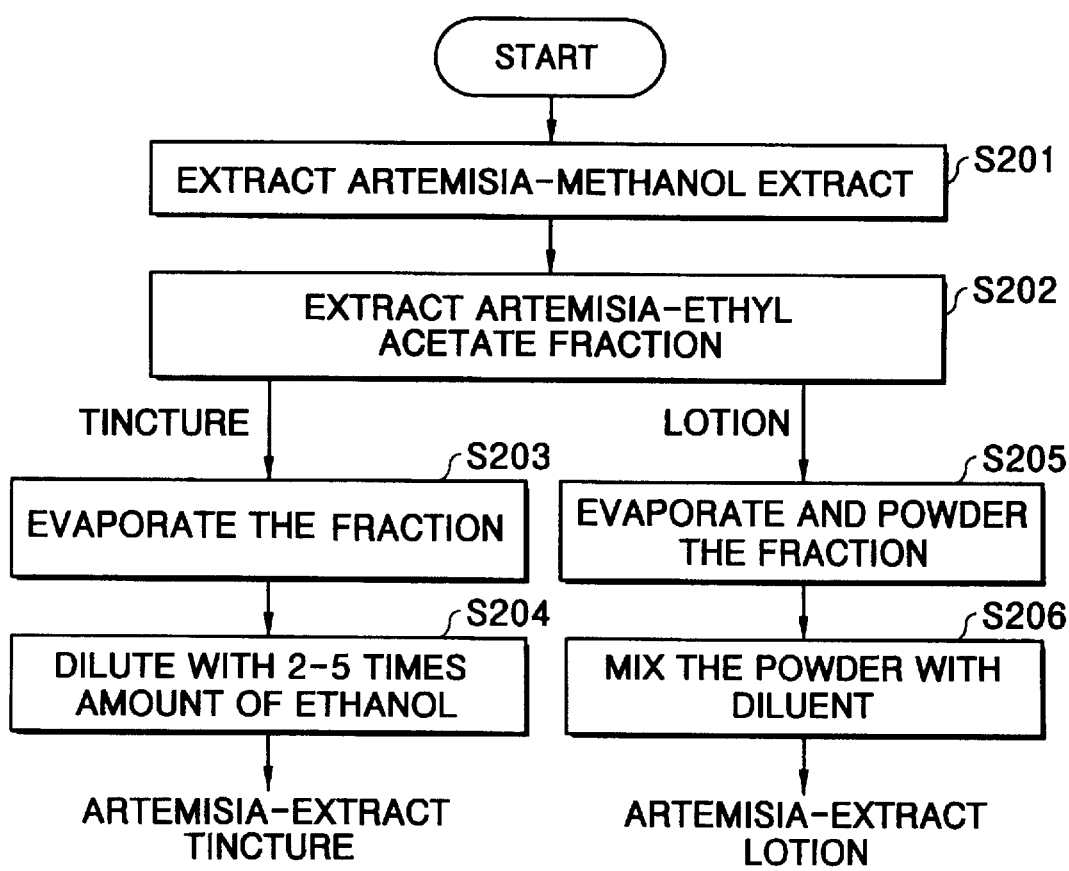
FIG. 2 is a flow chart for illustrating the second embodiment of the method of preparing pharmaceutical Moxa extract according to the present invention.

FIG. 2 is a flow chart showing another embodiment of the method of preparing pharmaceutical Moxa extract according to the present invention, which includes the steps of extracting Artemisia-methanol extract S201, extracting Artemisia-ethyl acetate fraction S202, and preparing pharmaceutical Moxa extract S203–S206.

When compared with FIG. 1, it can be easily seen that this embodiment further includes the step S202 of extracting the Artemisia-ethyl acetate fraction by suspending the Artemisia-ethyl acetate, extracted from the step of extracting the Artemisia-methanol extract S201, in water, then mixing the suspended extract with ethyl acetate, and then distilling the mixture with use of a fractional distiller. In the step of extracting Artemisia-ethyl acetate fraction S202, when the ethyl acetate mixture are distilled in the fractional distiller, phenolic compounds of the Artemisia can be simultaneously respectively extracted in upper and lower portions of the fractional distiller due to the difference of specific weight among the mixed components.

The steps of preparing pharmaceutical Moxa extract S203–S206 can obtain the pharmaceutical Moxa extract from the extracted fraction in S202. The pharmaceutical Moxa extract obtained in the steps S203–S206 is also in the form of having color but not leaving remnants after applied on the skin.

Particularly, in the steps S203, S204, after evaporating the Artemisia-ethyl acetate fraction S203, the Artemisia-extract tincture, which is possibly applied on the skin in a liquid type, can be made by diluting the dried Artemisia-ethyl acetate fraction with use of 2–5 times amount of ethanol relative to the weight of the dried Artemisia-ethyl acetate fraction S204.

In the steps of preparing pharmaceutical Moxa extract S205, S206, the Artemisia-ethyl acetate fraction is evaporated and then powdered into powder S205, and then diluent is mixed into the power S206 so to make the Artemisia-extract lotion which is possibly applied on the skin.

Figure 3:
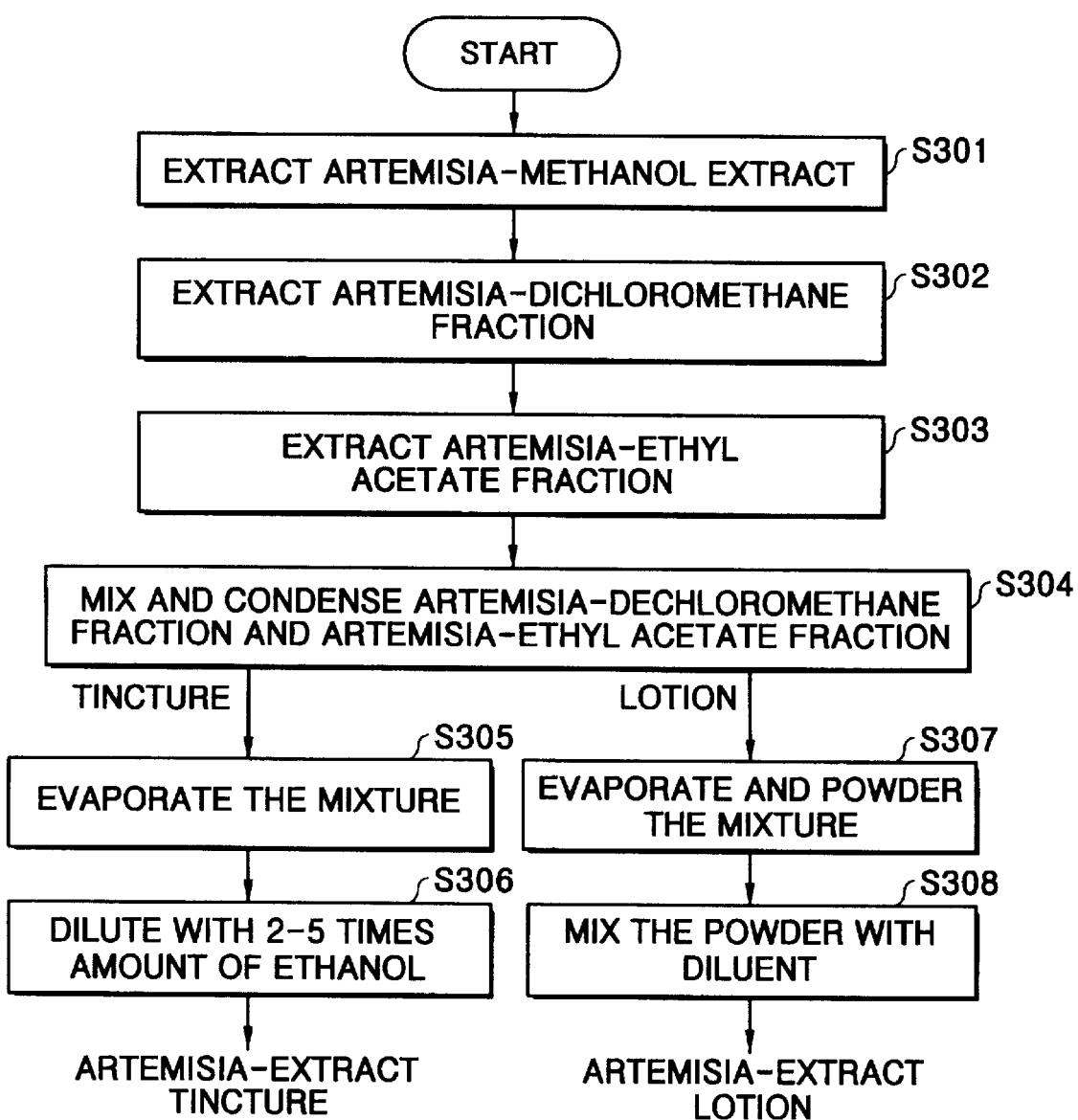
FIG. 3 is a flow chart for illustrating the third embodiment of the method of preparing pharmaceutical Moxa extract according to the present invention.

FIG. 3 is a flow chart showing another embodiment of the method of preparing pharmaceutical Moxa extract according to the present invention, which includes the steps of extracting the Artemisia-methanol extract S301, extracting Artemisia-dichloromethane fraction S302, extracting the Artemisia-ethyl acetate fraction S303, and preparing the pharmaceutical Artemisia extract S304–S308.

When compared with FIG. 2, it can be easily seen that the embodiment of FIG. 3 further includes the step of extracting the Artemisia-dichloromethane fraction S302 by suspending the Artemisia-methanol extract, extracted in the step S301, in water, then mixing the suspended extract with dichloromethane, and then distilling the mixture with use of the fractional distiller. In the step of extracting the Artemisia-dichloromethane fraction S302, when distilling the dichloromethane mixture in the fractional distiller, the Artemisia-dichloromethane fraction containing cineol and fatty acid can be extracted in a lower portion of the fractional distiller due to the difference of specific weight among the mixed components.

In the steps of preparing the pharmaceutical Artemisia extract S304–S308, the extracted Artemisia-dichloromethane fraction and Artemisia-ethyl acetate fraction are mixed and condensed S304, and then the pharmaceutical Moxa extract can be obtained from the condensed mixture. The pharmaceutical Moxa extract obtained at this time is also in the form of having color but not leaving remnants after being applied on the skin.

Particularly, in the steps of preparing the pharmaceutical Moxa extract S305, S306, after evaporating the condensed mixture of the Artemisia-dichloromethane fraction and the Artemisia-ethyl acetate fraction S305, the Artemisia-extract tincture, which is possibly applied on the skin in a liquid state, can be made by diluting the dried mixture with use of 2–5 times amount of ethanol relative to the weight of the dried mixture S306.

On the other hand, in the step of preparing the pharmaceutical Moxa extract S307, S308, the Artemisia-extract lotion, which is possibly applied on the skin, can be made by evaporating the condensed mixture of the Artemisia-dichloromethane fraction and the Artemisia-ethyl acetate fraction, then powdering the dried mixture S307, and mixing the power with diluent S308.

In the process of extracting the Artemisia-methanol extract in FIG. 1 to FIG. 3, though not shown in the figures, the Artemisia-methanol extract can be extracted by putting and sealing young leaves of the Artemisia in methanol, then firstly extracting Artemisia methanol after 24 hours at room temperature, putting and sealing the remaining young leaves of the Artemisia in methanol after extraction of the first Artemisia methanol, then secondly extracting Artemisia methanol after 24 hours at room temperature, putting and sealing the remaining young leaves of the Artemisia in methanol after extraction of the second Artemisia methanol, then thirdly extracting Artemisia methanol after 3 hours at 70–80° C., and then mixing and condensing all of the extracted Artemisia methanol made previously at three times.

In addition, in the process of extracting the Artemisia-methanol extract, medicine-mixed moxa, made by mixing the young leaves of the Artemisia with little medicinal stuffs including at least one of cinnamon cortex, dried ginger, clove, saussurea root, Korean aralia root, asarum, Angelicae Dahuricae root, orpiment, atractylis, myrrh, frankincense, akene, garlic, beeswax, and sulfur, can be used in order to improve pharmacological action of the moxa with use of the mixed medicinal stuffs and the Artemisia.

Figure 4:
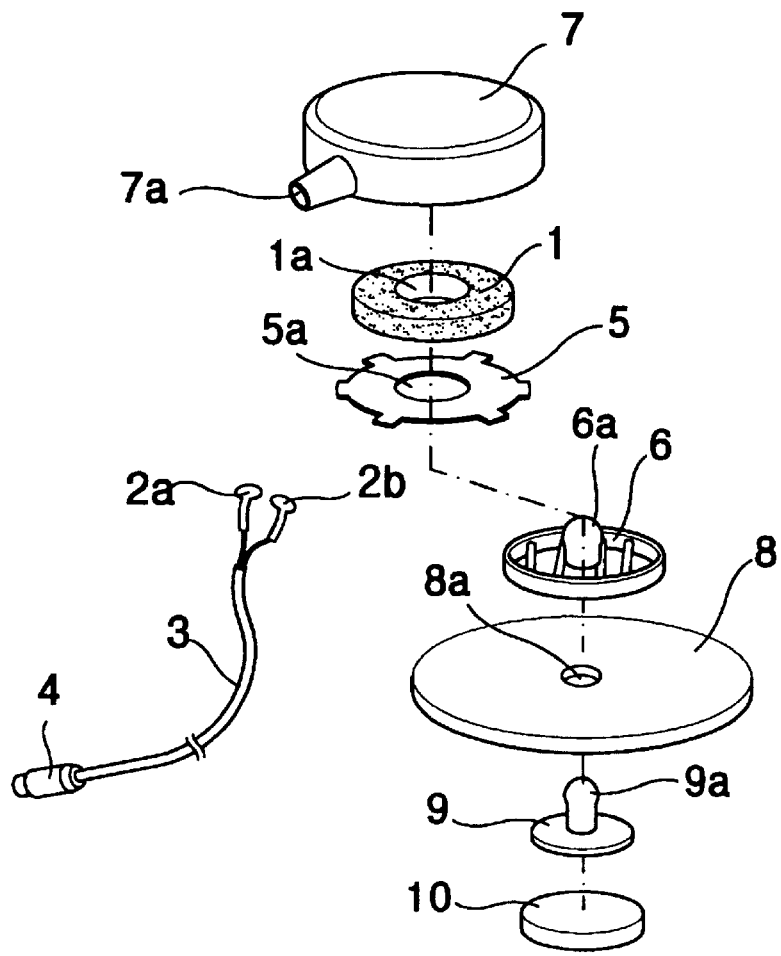
FIG. 4 is an exploded perspective view showing the first embodiment of an electrical moxibustion apparatus according to the present invention.
Figure 5:
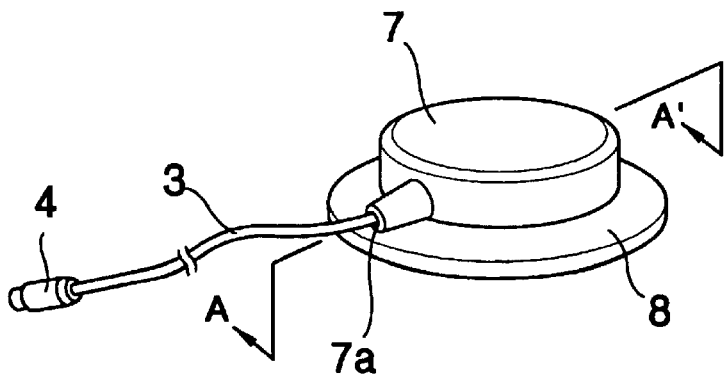
FIG. 5 is a perspective view for showing assembly state of FIG. 4.
Figure 6:
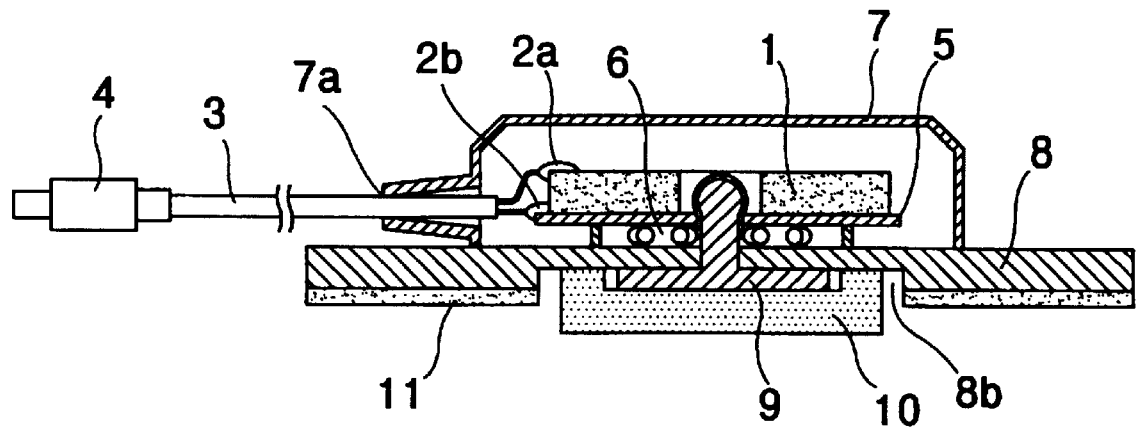
FIG. 6 is an enlarged section view taken along the line A–A' of FIG. 5.

FIG. 4 is an exploded perspective view showing the first embodiment of the electrical moxibustion apparatus according to the present invention, FIG. 5 shows assembly state of FIG. 4, and FIG. 6 is an enlarged section view taken along the line A–A' of FIG. 5.

As shown in the figures, the electrical moxibustion apparatus includes a power supply for supplying power from an external source, a heating unit for generating heat at a certain temperature when power is applied thereto, a heater fixing unit for fixing and supporting the heating unit, the heater fixing unit having first heat-transferring media for transferring heat from the heating unit to skin indirectly, an adiabatic unit for preventing heat of the heating unit from being dispersed to upper and side directions, the adiabatic unit forming a housing surrounding all upper and side portions of the heating unit and the heater fixing unit, and a moxibustion pad removably mounted to the heater fixing unit, the pad being indirectly heated by heat transferred from the heating unit through the first heat-transferring media, the pad having a synthetic resin pad in a certain area for covering the affected part and second heat-transferring media which is removably fixed to the first heat-transferring media.

For detailed description, the power supply includes a cable 3 and a power-connecting probe 4 for applying power from the external source, and two electrode terminals 2a, 2b connected through the probe and cable.

The heating unit includes a heating element 1 connected to upper and lower portions of the two electrode terminals 2a, 2b respectively for generating heat at constant temperature by using current from the electrode terminals. At this time, the heating element can be a ceramic resistance heater or a conductive polymer heater having a positive temperature coefficient (PTC). Such ceramic resistance heater can be made by mixing and sintering barium carbonate $BaCO_3$, strontium carbonate $SrCO_3$, yttrium oxide $Y_2O_3$, titan dioxide $TiO_2$ and silicon dioxide $SiO_2$, in which mixing proportions of barium carbonate $BaCO_3$, strontium carbonate $SrCO_3$, yttrium oxide $Y_2CO_3$, titan dioxide $TiO_2$ and silicon dioxide $SiO_2$ can be adjusted to form $(Ba_{0.8}Sr_{0.2})_{0.996}Y_{0.004}TiO_3+0.5_{wt}SiO_2$. In addition, the conductive polymer heater can be made by mixing an electrical conductor such as carbon black into polymeric materials such as polyethylene or rubber. At this time, considering that electrical properties, heat temperature, and melting point are determined according to mixing proportion thereof, the conductive polymer heater can be preferably a resistor for regulating heat temperature by adjusting the mixing proportion.

The adiabatic unit forms a housing surrounding all upper and side portions of the heating element 1, and includes a case 7 having a cable guiding groove 7a for fetching a cable connected to the heating element 1.

The heater fixirg unit includes a first heat-transferring media 6 for transferring heat from the heating element 1 to the skin, and a fixing plate 5 for facilitating soldering in order to connect an external cable to the heating element 1. The first heat-transferring media 6 includes a first button contact 6a formed on a center portion thereof for the purpose of attachment and detachment of the removable moxibustion pad, and the fixing plate 5 includes a through hole 5a for easily fixing the first heat-transferring media 6 by guiding the first button contact 6a. Also, the heating element 1 preferably includes a through hole 1a for guiding the first button contact 6a. Therefore, the first button contact 6a is guided along the two through holes 5a, 1a so that the first heat-transferring media 6 can be sequentially installed to the fixing plate 5 and the heating element 1, then transferring heat from the heating element 1.

In addition, the removable moxibustion pad includes a synthetic resin pad 8 in form of a sponge rubber plate having a certain contact area with the skin for covering the affected part for moxibustion, second heat-transferring media 9 removably fixed to the first heat-transferring media 6 through the synthetic resin pad 8 therebetween, and a liquid permeable membrane 10 attached to the second heat-transferring media 9, through which the pharmaceutical Moxa extract can be injected with use of sponge materials. The second heat-transferring media 9 includes second button contact 9a formed on a center portion thereof so to be detachably attached to the first button contact 6a of the first heat-transferring media 6, and a through hole 8a is formed on a center portion of the synthetic resin pad 8 in order to guide the second button contact 9a. Therefore, the second heat-transferring media 9 fixes the synthetic resin pad 8 by guided along the through hole 8a of the synthetic resin pad 8, and is then combined to the first button contact 6a of the first heat-transferring media 6 so that heat can be transferred to the second heat-transferring media 9.

Under the synthetic resin pad, an end-shielding groove 8b is formed toward the skin such that the second heat-transferring media 9 and the liquid permeable membrane 10 can be interposed thereinto so to be inserted to a depth of surrounding upper and side portions of the liquid permeable membrane 10. Therefore, because the sponge rubber plate surrounds upper and rim of the second heat-transferring media 9 and the liquid permeable membrane 10, heat can be transferred throughout the whole synthetic resin pad, which enhances heat transfer.

In addition, the removable moxibustion pad inserts the liquid permeable membrane 10, made of a sponge membrane through which the pharmaceutical Moxa extract can be injected, into the end-shielding groove 8b such that the liquid permeable membrane 10 can be indirectly heated. After that, when injecting the pharmaceutical Moxa extract into the liquid permeable membrane 10, moxibustion can be operated by the pharmaceutical Moxa extract. At this time, the removable moxibustion pad can be repeatedly used by injecting required amount of the pharmaceutical Moxa extract into the liquid permeable membrane 10, or can be disposable after first time use with use of the first and second button contacts 6a, 9a.

In the removable moxibustion pad, adhesive 11 (see FIG. 5) is also applied on a skin-contact surface of the synthetic resin pad in order to increase adhesion between the synthetic resin pad and the skin.

Moxibustion remedy using the electrical moxibustion apparatus constructed as above and the pharmaceutical Moxa extract prepared according to the present invention is as follows. At first, the second heat-transferring media 9 and the synthetic resin pad 8 are combined after guiding the second button contact 9a of the second heat-transferring media 9 into the through hole 8a of the synthetic resin pad 8. The liquid permeable membrane 10 is then attached to the second heat-transferring media 9. The adhesive 11 is then applied to rim of the contact area of the synthetic resin pad 8, then forming the removable moxibustion pad. After that, when injecting required amount of the pharmaceutical Moxa extract into the liquid permeable membrane 10, the liquid permeable membrane 10 keeps the liquid-phase pharmaceutical Moxa extract owing to its sponge materials. Then, when putting the removable moxibustion pad on the affected parts, the adhesive 11 becomes in contact with the skin and the synthetic resin pad 8 becomes fixed on the affected parts.

Combining the removable moxibustion pad and the heater fixing unit with use of each button contact 6a, 9a of the first and second heattransferring media 6, 9 makes the electrical moxibustion apparatus assembled. After that, when applying power through the probe 4 of the apparatus, current flows in the heating element 1 through the two electrode terminals 2a, 2b in the apparatus, so to generate heat. With generating heat, the pharmaceutical Moxa extract injected in the liquid permeable membrane become melted such that melted moxa components can be permeated into the skin, which provides moxibustion effect. After that, the electrical moxibustion apparatus maintains the positive temperature coefficient (PTC) till a specific temperature, for example 100° C. At this time, the heating element 1 generates heat at a certain predetermined temperature according to mixing proportion of the compounded materials. Therefore, the pharmacological components of the moxa, applied on the skin, become permeated into skin tissues so to generate pharmacological action of the Moxa and hyperthermia action, which makes the moxibustion treatment simple.

Figure 7:
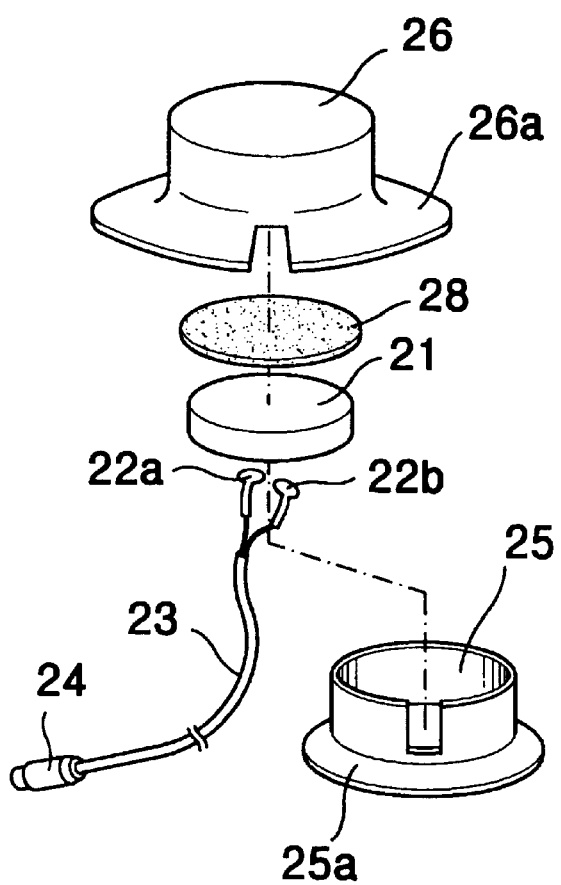
FIG. 7 is an exploded perspective view showing the second embodiment of the electrical moxibustion apparatus according to the present invention.
Figure 8:
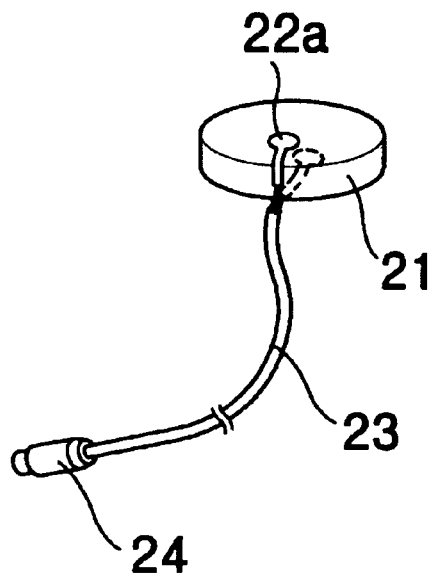
FIGS. 8 to 10 are perspective views for sequentially showing assembly process of FIG. 7, respectively.
Figure 9:
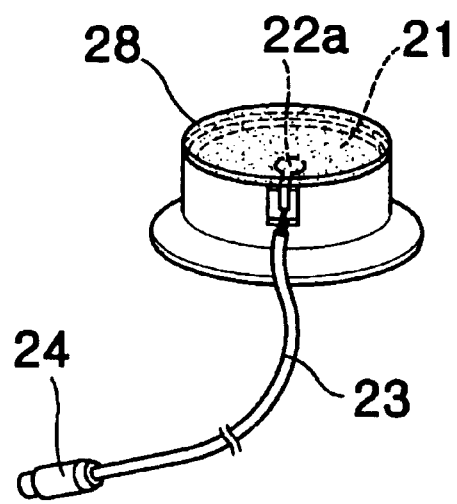
Figure 10:
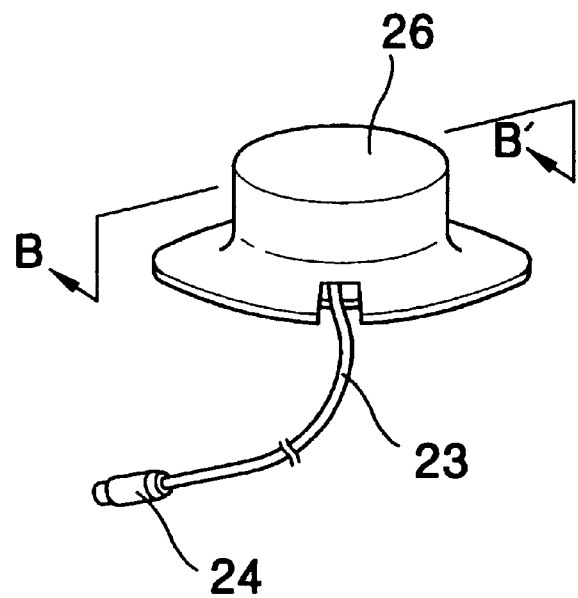
Figure 11:
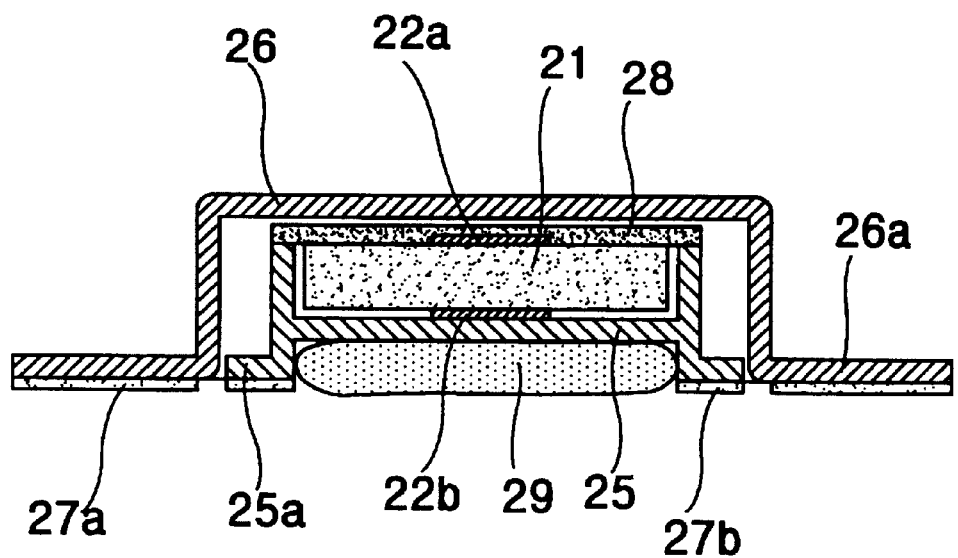
FIG. 11 is an enlarged section view taken along the line B–B' of FIG. 10.

FIG. 7 is an exploded perspective view of the second embodiment of the electrical moxibustion apparatus according to the present invention, FIG. 8 to FIG. 10 are perspective views sequentially showing assembling process of FIG. 7, and FIG. 11 is an enlarged view taken along the line B–B' in FIG. 10. As shown in the figures, the electrical moxibustion apparatus includes a power supply for supplying power from an external source, a heating unit having two electrode terminals, which generates heat at a certain temperature when power is applied through the terminals, a heater fixing unit, molded with insulating materials, having a case having a seating groove opened upwardly for seating the heating unit thereon in order to fix and support the heating unit safely with use of the case and transfer heat from the heating unit to skin indirectly, and an adiabatic unit for preventing heat of the heating unit from being dispersed to upper and side directions, the adiabatic unit forming a housing surrounding all upper and side portions of the heating unit and the heater fixing unit.

The power supply includes a cable 23 and a power-connecting probe 24 for applying power from the external source, and two electrode terminals 22a, 22b connected through the probe and cable.

The heating unit includes a PTC resistor 21 having the two electrode terminals 22a, 23b at upper and lower portions respectively for generating heat at constant temperature by using current from the electrode terminals.

The PTC resistor 21 can be made by mixing and sintering barium carbonate $BaCO_3$, strontium carbonate $SrCO_3$, yttrium oxide $Y_2O_3$, titan dioxide $TiO_2$ and silicon dioxide $SiO_2$, in which mixing proportions of barium carbonate $BaCO_3$, strontium carbonate $SrCO_3$, yttrium oxide $Y_2O_3$, titan dioxide $TiO_2$ and silicon dioxide $SiO_2$ can be adjusted to form $(Ba_{0.8}Sr_{0.2})_{0.996}Y_{0.004}TiO_3+0.5_{wt}SiO_2$. The PTC resistor 21 can regulate heat temperature by adjusting mole ratio of barium Ba and strontium Sr so as to form curie-temperature at a range of 40° C.–60° C. which is not harmful to human body in hyperthermia and moxibustion remedy. At this time, because moxibustion temperature required to body may be different according to diathesis of the person, the heat temperature is variable in such range.

Though not shown in the figures, the heating unit can include a nichrome wire heater instead of the PTC resistor.

In this case, the heating unit may further include a switching unit for maintaining heating temperature in a certain range by intermitting current, supplied to the nichrome wire heater, according to a temperature of the nichrome wire heater.

The heater fixing unit includes a seating groove opened upwardly for seating the heating unit, and a case body for surrounding whole surface of the PTC resistor. The case body also has a cable guiding groove formed at a certain side thereof for fetching the cable connected to the PTC resistor. In the heater fixing unit, therefore, the seating groove and the case body constitute a case 25 with heat resistance materials which indirectly transfers heat from the PTC resistor to the skin by molding the surface of the PTC resistor with use of the insulating materials in form of seating the PTC resistor 21 on the case body and then surrounding the surface of the PTC resistor. The case body can be particularly made of heat resistance resin, impassive to heat, and coated with insulating materials such as silicon in order to insulate the skin from the resistor when the case body contacts with the skin. The case 25 also includes a detachable double-side adhesive tape applied on a skin-contact surface thereof in order to increase adhesion between the skin and a lower surface thereof. In addition, in order to broaden contact area between the lower surface and the skin, a brim 25a can be formed along lower side verges of the case. Furthermore, in order to increase adhesion with the skin, the detachable double-side adhesive tape 27b can also be attached on the brim 25a. The heater fixing unit may also include an end-shielding groove (not indicated with numeral in the drawing) opened toward the skin on an opposite side to the seating groove of the case 25 with a certain depth in order to insert the pharmaceutical Moxa extract thereinto.

As an adiabatic means, a detachable holder 26 can be assembled and adhered onto the case 25 in form of surrounding all upper and side portions of the resistor 21 in order to prevent heat, generated from the resistor, from being dispersed to outside. The holder 26, used for increasing insulation with use of thin sponge materials, can include a brim 26a formed along lower side verges thereof in order to broaden contact area with the skin. In addition, a detachable double-side adhesive tape 27a can be adhered to the brim 26a in order to increase adhesion with the skin.

In addition, though not shown in the figures, the electrical moxibustion apparatus of the present invention can be connected to a main body for regulating voltage applied to the apparatus. Besides, the main body may include a plurality of connecting terminals for connecting probes of a plurality of electrical moxibustion apparatuses such that many moxibustion apparatuses can be used at the same time. Furthermore, a connecting receptacle or a distribution box in order to increase number of the moxibustion apparatus used at the same time and expand radius of use.

The process of operating moxibustion remedy using the electrical moxibustion apparatus and the pharmaceutical Moxa extract is as follows. At first, an operator applies the pharmaceutical Moxa on the affected parts, and then puts the electrical moxibustion apparatus thereon, which makes the double-side adhesive tapes 27a, 27b of the electrical moxibustion apparatus contacted and fixed on the skin at the same time. Then, when connecting the apparatus to the power source through the probe 24, current flows in the PTC resistor 21 through the two electrode terminals 22a, 22b in the apparatus such that the PTC resistor generates heat. At this time, the PTC resistor 21 generates heat at a certain predetermined temperature according to mole ratio of the compounds. Therefore, crude drug components of the moxa applied on the skin penetrates the skin so to provide pharmacological action of the moxa with use of the mixed medicinal stuffs and the Moxa, which makes the moxibustion remedy simple.

By using the present invention as described above, the moxibustion remedy can be easily operated by using a quite new manner which applies power using button contact with a lead wire of the heat generating unit after attaching the moxibustion pad, containing the pharmaceutical Moxa extract, onto the affected parts in a similar method of attaching several skin electrodes on limbs and thorax in case of writing electrocardiogram.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. An apparatus for electrical moxibustion using pharmaceutical Moxa extract comprising:

heating means for generating heat at a certain temperature when power is applied thereto;

fixing means for fixing and supporting the heating means, the fixing means having first heat-transferring media for transferring heat from the heating means to skin indirectly and a fixing plate for electrically connecting a lead wire, used for applying power to the heating means;

adiabatic means for preventing heat of the heating means from being dispersed to upper and side directions, the adiabatic means forming a housing surrounding all upper and side portions of the heating means and the fixing means; and moxibustion pad means containing the pharmaceutical Moxa extract and being removably mounted to the fixing means, the pad means being indirectly heated by heat transferred from the heating means through the first heat-transferring media, the pad means having a synthetic resin pad in a certain area for covering the affected part and second heat transferring media, which is removably fixed to the first heat-transferring media and a liquid permeable membrane having a characteristic of penetrating liquid therethrough under the synthetic resin pad in order to inject pharmaceutical Moxa extract; and further wherein, first button contact means is formed on a center portion of the first heat-transferring media for the purpose of attachment and detachment with the removable moxibustion pad means, and through holes are formed on the heating means and the fixing plate, respectively, in order to guide the first button contact means.

2. An apparatus for electrical moxibustion comprising:

heating means for generating heat at a certain temperature when power is applied thereto;

fixing means for fixing and supporting the heating means, the fixing means having first heat-transferring media for transferring heat from the heating means to skin indirectly;

adiabatic means for preventing heat of the heating means from being dispersed to upper and side directions, the adiabatic means forming a housing surrounding all upper and side portions of the heating means and the fixing means; and moxibustion pad means removably mounted to the fixing means, the pad means being indirectly heated by heat transferred from the heating means through the first heat-transferring media, the pad means having a synthetic resin pad in a certain area for covering the affected part and second heat-transferring media which is removably fixed to the first heat-transferring media; and wherein the heating means comprises a ceramic resistance heater having a positive temperature coefficient (PTC).

3. An apparatus for electrical moxibustion comprising: heating means for generating heat at a certain temperature when power is applied thereto; fixing means for fixing and supporting the heating means, the fixing means having first heat-transferring media for transferring heat from the heating means to skin indirectly;

adiabatic means for preventing heat of the heating means from being dispersed to upper and side directions, the adiabatic means forming a housing surrounding all upper and side portions of the heating means and the fixing means; and moxibustion pad means removably mounted to the fixing means, the pad means being indirectly heated by heat transferred from the heating means through the first heat-transferring media, the pad means having a synthetic resin pad in a certain area for covering the affected part and second heat-transferring media which is removably fixed to the first heat-transferring media; and further wherein, the heating means comprises a ceramic resistance heater having a positive temperature coefficient (PTC); and wherein the ceramic resistance heater utilizes positive temperature coefficient resistor in which barium carbonate $BaCO_3$, strontium carbonate $SrCO_3$, Yttrium oxide $Y_2O_3$, titanium dioxide $TiO_2$, and silicon dioxide $SiO_2$, are mixed and sintered to form a curie-temperature at a certain temperature range.

4. The apparatus for electrical moxibustion as claimed in claim 1, wherein the heating means comprises a conductive polymer heater which is made by mixing conductors into polymeric materials.

5. The apparatus for electrical moxibustion as claimed in claim 4, wherein the conductive polymer heater is made by mixing carbon black into polymeric materials such as polyethylene or rubber.

6. The apparatus for electrical moxibustion as claimed in claim 1, further comprising a fixing plate for electrically connecting a lead wire, used for applying power to the heating means.

7. An apparatus for electrical moxibustion comprising:

heating means for generating heat at a certain temperature when power is applied thereto;

fixing means for fixing and supporting the heating means, the fixing means having first heat-transferring media for transferring heat from the heating means to skin indirectly;

adiabatic means for preventing heat of the heating means from being dispersed to upper and side directions, the adiabatic means forming housing surrounding all upper and side portions of the heating means and the fixing means; and moxibustion pad means removably mounted to the fixing means, the pad means being indirectly heated by heat transferred from the heating means through the first heat-transferring media, the pad means having a synthetic resin pad in a certain area for covering the affected part and second heat-transferring media which is removably fixed to the first heat-transferring media; and further wherein, first button contact means is formed on a center portion of the first heat-transferring media for the purpose of attachment and detachment with the removable moxibustion pad means, and a through hole is formed on the heating means and the fixing plate in order to guide the first button contact means; and wherein the removable moxibustion pad means comprises:

second button contact means formed on a center portion of the second heat-transferring media so to being detachably attached to the first button contact means of the first heat-transferring means; and a through hole formed on a center portion of the synthetic resin pad in order to guide the second button contact means.

8. The apparatus for electrical moxibustion as claimed in claim 1, wherein the removable moxibustion pad means comprises a liquid permeable membrane having a characteristic of penetrating liquid therethrough under the synthetic resin pad in order to inject pharmaceutical Moxa extract.

9. The apparatus for electrical moxibustion as claimed in claim 8, wherein the liquid permeable membrane is a sponge membrane.

10. An apparatus for electrical moxibustion comprising:

heating means for generating heat at a certain temperature when power is applied thereto;

fixing means for fixing and supporting the heating means, the fixing means having first heat-transferring media for transferring heat from the heating means to skin indirectly;

adiabatic means for preventing heat of the heating means from being dispersed to upper and side directions, the adiabatic means forming a housing surrounding all upper and side portions of the heating means and the fixing means; and moxibustion pad means removably mounted to the fixing means, the pad means being indirectly heated by heat transferred from the heating means through the first heat-transferring media, the pad means having a synthetic resin pad in a certain area for covering the affected part and second heat-transferring media which is removably fixed to the first heat-transferring media, wherein, the removable moxibustion pad means comprises a liquid permeable membrane having a characteristic of penetrating liquid therethrough under the synthetic resin pad in order to inject pharmaceutical Moxa extract; and wherein the removable moxibustion pad means has an end-shielding groove formed under the synthetic resin pad toward skin with a certain depth in order to insert the second heat-transferring media and the liquid permeable membrane thereinto.

11. The apparatus for electrical moxibustion as claimed in claim 1, wherein the synthetic resin pad is a sponge rubber plate.

12. The apparatus for electrical moxibustion as claimed in claim 1, wherein the removable moxibustion pad means includes adhesive applied on a skin-contact surface of the synthetic resin pad in order to increase adhesion between the synthetic resin pad and the skin.

13. The apparatus for electrical moxibustion as claimed in claim 12 wherein the heating means has two electrode terminals, which generates heat at a certain temperature when power is applied from the terminals;

the fixing means forming a case having a seating groove opened upwardly for seating the heating means thereon, the fixing means fixing and supporting the heating means safely with use of the case, the fixing means transferring heat from the heating means to skin indirectly, wherein the fixing means is formed by molding insulating materials with coating inside of the seating groove with insulating materials and seating the heating means upon the seating groove in order to be insulated from the heating means.

* * * * *

UNITED STATES PATENT AND TRADEMARK OFFICE
CERTIFICATE OF CORRECTION

PATENT NO.     : 6,253,104 B1
DATED          : June 26, 2001
INVENTOR(S)    : Jo It is certified that error appears in the above-identified patent and that said Letters Patent is hereby corrected as shown below:

<u>Title page,</u>
Item [75], Inventor, "Bong Kwon Jo" should read -- Bong Kwan Jo --

Signed and Sealed this

Third Day of June, 2003

JAMES E. ROGAN
*Director of the United States Patent and Trademark Office*